(12) United States Patent
Takahashi (10) Patent No.: US 10,137,113 B2
(45) Date of Patent: Nov. 27, 2018

(54) 5-HT4 RECEPTOR AGONIST AS A PROKINETIC AGENT

(75) Inventor: Nobuyuki Takahashi, Aichi (JP)

(73) Assignee: RaQualia Pharma Inc., Aichi (JP)

( * ) Notice: Subject to any disclaimer, the term of this patent is extended or adjusted under 35 U.S.C. 154(b) by 133 days.

(21) Appl. No.: 14/006,550

(22) PCT Filed: Mar. 23, 2012

(86) PCT No.: PCT/JP2012/002042
§ 371 (c)(1),
(2), (4) Date: Oct. 28, 2013

(87) PCT Pub. No.: WO2012/127878
PCT Pub. Date: Sep. 27, 2012

(65) Prior Publication Data
US 2014/0051726 A1   Feb. 20, 2014

(30) Foreign Application Priority Data
Mar. 23, 2011   (JP) ................. 2011-065067

(51) Int. Cl.
| A61K 31/435 | (2006.01) |
| A61K 31/454 | (2006.01) |
| A61K 45/06  | (2006.01) |
| C07D 413/14 | (2006.01) |

(52) U.S. Cl.
CPC .......... *A61K 31/435* (2013.01); *A61K 31/454* (2013.01); *A61K 45/06* (2013.01); *C07D 413/14* (2013.01)

(58) Field of Classification Search
CPC .... A61K 31/435; A61K 31/454; A61K 45/06; C07D 413/14
See application file for complete search history.

(56) References Cited

U.S. PATENT DOCUMENTS

| 5,280,030 A | 1/1994 | Jegham et al. |
| 2003/0059374 A1 | 3/2003 | Lehman et al. |
| 2005/0090554 A1 | 4/2005 | Devane et al. |
| 2014/0051726 A1 | 2/2014 | Takahashi |

FOREIGN PATENT DOCUMENTS

| EP | 0602242 A1 | 6/1994 |
| RU | 2008129615 A | 1/2010 |
| WO | WO-9304063 A1 | 3/1993 |
| WO | WO-2006090224 A1 | 8/2006 |
| WO | WO-2007071394 A2 | 6/2007 |
| WO | WO-2012127878 A1 | 9/2012 |

OTHER PUBLICATIONS

International Search Report in corresponding PCT/JP2012/002042 dated May 15, 2012.
Bockaert et al., "5-HT$_4$ Receptors Potential Therapeutic Implications in Neurology and Psychiatry", *CNS Drugs 1*, pp. 6-15 (1994).
Bouras et al., "Selective Stimulation of Colonic Transit by the Benzofuran 5HT$_4$ Agonist, in Healthy Humans", *Gastroenterology*, pp. 682-686 (1999).
Manini et al., "Effects of Velusetrag (TD-5108) on Gastrointestinal Transit and Bowel Function in Health and Pharmacokinetics in Health and Constipation", *Neurogastroenterol Motil*, pp. 42-$_e$8 (2010).
Camilleri et al., "Pharmacodynamic Effects of a Novel Prokinetic 5-HT$_4$ Receptor Agonist, ATI-7505, in Humans", *Neurogastroenterol Motil*, pp. 30-38 (2007).
Bockaert et al., "The 5-HT$_4$ Receptor: A Place in the Sun", *TiPS*, pp. 141-145 (1992).
Ford et al., "The 5-HT$_4$ Receptor", *Medicinal Research Reviews*, pp. 633-662 (1993).
Gullikson et al., "Gastrointestinal Motility Responses to the S and R Enantiomers of Zacopride, a 5-HT$_4$ Agonist and 5-HT$_3$ Antagonist", *Drug Development Research*, pp. 405-417 (1992).
Eglen et al., "Central 5-HT$_4$ Receptors", *TiPS*, pp. 391-398 (1995).
Romanelli et al., "Synthesis and Biological Activity of a Series of Aryl Tropanyl Esters and Amides Chemically Related to 1H-Indole-3-Carboxylic Acid Endo 8-Methyl-8-Azabicyclo[3.2.1]Oct-3-yl Ester", *Arzheim Forsch./Drug Res.*, pp. 913-918 (1993).
Kaumann et al., "A 5-HT$_4$-like Receptor in Human Right Atrium", *Naunyn-Schmiedeberg's ArchPharmacol*, pp. 150-159 (1991).
Bouras et al., "Prucalopride Accelerates Gastrointestinal and Colonic Transit in Patients with Constipation Without a Rectal Evacuation Disorder", *Gastroenterology*, pp. 354-360 (2001).
Degen et al., "Tegaserod, a 5-HT4 Receptor Partial Agonist, Accelerates Gastric Emptying and Gastrointestinal Transit in Healthy Male Subjects", *Aliment Pharmacol Ther*, pp. 1745-1751 (2001).
Mine et al., Comparison of Effect of Mosapride Citrate and Existing 5-HT$_4$ Receptor Agonists on Gastrointestinal Motility In Vivo and In Vitro, J. Pharmacol. Exp. Ther., vol. 283, No. 3. pp. 1000-1008, 1997.
Office Action in corresponding Chinese application No. 201280014638.X dated Dec. 16, 2015.

(Continued)

*Primary Examiner* — Sarah Pihonak
*Assistant Examiner* — Jason Deck
(74) *Attorney, Agent, or Firm* — Marshall, Gerstein & Borun LLP (57) ABSTRACT

This invention relates to Compound A or a pharmaceutically acceptable salt thereof with 5-HT4 agonistic activities, which is useful in the treatment of gastrointestinal diseases. This invention also relates to a pharmaceutical composition for the treatment of gastrointestinal diseases which comprises a therapeutically effective amount of Compound A or a pharmaceutically acceptable salt thereof. Further this invention relates to a method for the treatment of gastrointestinal diseases in an animal subject including a mammalian subject, which comprises administering to the animal subject including a mammalian subject Compound A or a pharmaceutically acceptable salt thereof.

10 Claims, 4 Drawing Sheets

(56) References Cited

OTHER PUBLICATIONS

U.S. Appl. No. 15/306,914, filed Oct. 26, 2016.
International Search Report and Written Opinion for Application No. PCT/JP2015/002478, dated Aug. 18, 2015.
Eamonm MM Quigley, "Pharmacotherapy of gastroparesis", *Expert Opin. Pharmacotherapy*, vol. 1, No. 5, pp. 881-887, 2000.
Maeyer et al., "5-HT4 receptor agonists: similar but not the same", *Neurogastroenterol Motil*, vol. 20, pp. 99-112, 2008.
Soykan et al., "Demography, Clinical Characteristics, Psychological and Abuse Profiles, Treatment, and Long-Term Follow-up of Patients with Gastroparesis", *Dig. Dis. Sci.*, vol. 43, No. 11, 1998.
Hiba et al., "Is There a Difference in the Prevelance of Gastrointestinal Symptoms Between Type I and Type II Diabetics?", *Gastroenterology*, vol. 4, pp. A79, 1999.
McCallum et al., "Diabetic and Nondiabetic Gastroparesis", *Current Treatment Options Gastroenterology*, vol. 1, pp. 1-7, 1998.
Sturm et al., "Prokinetics in Patients with Gastroparesis: A Systematic Analysis", *Digestion*, vol. 60, pp. 422-427, 1999.
Jones et al., "Predictors of Delayed Gastric Emptying in Diabetes", *Diabetes Care*, vol. 24, No. 7, pp. 1264-1269, 2001.
Parkman et al., "Treatment of Patients with Diabetic Gastroparesis", *Gastroenterology & Hepatology*, vol. 6, pp. 1-16, 2010.
Decision of Grant in corresponding Russian Patent Application No. 2013147196 dated May 31, 2016.

5-HT4 RECEPTOR AGONIST AS A PROKINETIC AGENT

TECHNICAL FIELD

This invention relates to 4-{[4-({[4-(2,2,2-trifluoroethoxy)-1,2-benzisoxazol-3-yl]oxy}methyl)piperidin-1-yl]m ethyl}tetrahydro-2H-pyran-4-carboxylic acid (hereinafter, referred to as 'Compound A') for use in therapeutic treatment of the human body. In particular, it relates to Compound A with selective 5-HT4 receptor agonism which is useful for treating gastrointestinal diseases, or preventing or delaying the onset or the progression of gastrointestinal diseases.

This invention also relates to a pharmaceutical composition for the treatment of gastrointestinal diseases which comprises a therapeutically effective amount of Compound A or a pharmaceutically acceptable salt thereof. This invention relates to a method for the treatment of gastrointestinal diseases in an animal subject including a mammalian subject, which comprises administering to the animal subject including a mammalian subject Compound A or a pharmaceutically acceptable salt thereof. Further this invention relates to a method for the treatment of gastrointestinal diseases in an animal subject including a mammalian subject, which comprises administering to the animal subject including a mammalian subject in need a therapeutically effective amount of Compound A or a pharmaceutically acceptable salt thereof.

BACKGROUND ART

In general, 5-HT4 receptor agonists are found to be useful for the treatment of a variety of diseases such as gastroesophageal reflux disease (GERD), gastrointestinal disease, gastric motility disorder, non-ulcer dyspepsia, functional dyspepsia (FD), irritable bowel syndrome (IBS), constipation, dyspepsia, esophagitis, gastroesophageal disease, gastritis, nausea, central nervous system disease, Alzheimer's disease (AD), cognitive disorder, emesis, migraine, neurological disease, pain, cardiovascular disorders such as cardiac failure and heart arrhythmia, and apnea syndrome (See NPL 1; NPL 2; NPL 3; NPL 4; NPL 5; NPL 6; and NPL 7).

It is clear that the drugs with 5-HT4 receptor agonistic activity act as a prokinetic agent.

However the tissue specific activity in the upper or lower gastrointestinal tract has also been shown in 5-HT4 agonists such as cisapride, mosapride, prucalopride and tegaserod. Namely, mosapride and cisapride selectively enhanced upper gastrointestinal (GI) motility rather than lower GI motility, which resulted in being on the market as prokinetic agents.

On the other hand, prucalopride (NPL 8) and tegaserod (NPL 9) enhanced lower GI motility, which resulted in as the clinical use of constipation and/or constipation-predominant IBS (C-IBS). In addition, prucalopride (NPL 8) has been suggested to selectively stimulate colonic transit in healthy humans without altering gastric empting or small bowel transit (NPL 10).

Further, velusetrag (TD-5108) (NPL 11) and naronapride (ATI-7505) (NPL 12) which are being developed are falls in the constipation categories.

In medial front, a large population of patients with functional bowel disorders have frequently overlapping symptoms that affect both the upper and lower GI tract. Actually, IBS is frequently seen in association with GERD. Unfortunately there are no drugs having both upper and lower GI motilities in a same extent. Therefore, such an ideal drug showing stimulatory effects on both upper and lower GI motilities in a single administration is highly desired in many patients with GI diseases.

The present inventors in order to solve the problems as above have discovered that Compound A with 5-HT4 agonism exerts stimulatory effects on antral (upper) and colonic (lower) motility at the same dose. Therefore, this invention relates to the first example of the compound which demonstrates stimulatory effects both upper and lower GI motilities clearly in a same extent. In addition, the effects on GI motility of Compound A are much higher (more than 100 times) than those of other 5-HT4 agonists as shown in the working examples described in this specification. These profiles show that Compound A is valuable and feasible alternative to other prokinetic agents for patients suffering from functional constipation and C-IBS with upper GI symptoms such as dyspepsia or heartburn.

CITATION LIST

Non Patent Literature

{NPL 1}
Bockaert J. et al., *TiPs* 13; 141-45, 1992
{NPL 2}
Ford A. P et al., *Med. Res. Rev.* 13: 633-62, 1993
{NPL 3}
Gullikson G. W. et al., *Drug Dev. Res.* 26; 405-17, 1992
{NPL 4}
Richard M. Eglen et al., *TiPs* 16; 391-98, 1995
{NPL 5}
Bockaert J. et al., *CNS Drugs* 1; 6-15, 1994
{NPL 6}
Romanelli M. N. et al., *Arzheim Forsch./Drug Res.*, 43; 913-18, 1993
{NPL 7}
Kaumann A. J. et al., *Naunyn-Schmiedebergs Arch Pharmacol.*, 344; 150-59, 1991
{NPL 8}
Bouras E. P. et al., Gastroenterology. 2001 February; 120 (2):354-60.
{NPL 9}
Degen L. et al., Aliment Pharmacol Ther. 2001 November; 15(11):1745-51.
{NPL 10}
Bauras E. P. et al., Gut, 1999, 44, 682-686
{NPL 11}
Manini M. L. et al., Neurogastroenterol Motil. 2010 January; 22(1):42-9, e7-8. Epub 2009 Aug. 18.
{NPL 12}
Camilleri M. et al., Neurogastroenterol Motil. 2007 January; 19(1):30-8.

SUMMARY OF INVENTION

Technical Problem

An object of the present invention is to provide Compound A for use in therapeutic treatment of the human body. In particular, an object of the present invention is to provide Compound A with selective 5-HT4 receptor agonism which is useful for treating gastrointestinal diseases, or preventing or delaying the onset or the progression of gastrointestinal diseases.

In addition, an object of the present invention is to provide a pharmaceutical composition for the treatment of gastrointestinal diseases which comprises a therapeutically effective amount of Compound A or a pharmaceutically acceptable salt thereof, a method for the treatment of gastrointestinal diseases in an animal subject including a mammalian subject, which comprises administering to the animal subject including a mammalian subject Compound A or a pharmaceutically acceptable salt thereof, and a method for the treatment of gastrointestinal diseases in an animal subject including a mammalian subject, which comprises administering to the animal subject including a mammalian subject in need a therapeutically effective amount of Compound A or a pharmaceutically acceptable salt thereof.

Solution to Problem

The gist of the present invention is as follows:

[1] use of 4-{[4-({[4-(2,2,2-trifluoroethoxy)-1,2-benzisoxazol-3-yl]oxy}methyl)-piperidin-1-yl]methyl}tetrahydro-2H-pyran-4-carboxylic acid or a pharmaceutically acceptable salt thereof in the manufacture of a medicament for the treatment of gastrointestinal diseases in an animal subject including a mammalian subject;

[2] the use of item [1], wherein 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid or a pharmaceutically acceptable salt thereof is used in combination with one or more additional compounds known to be useful in the treatment or prevention of gastrointestinal diseases or the symptoms thereof;

[3] a pharmaceutical composition for the treatment of gastrointestinal diseases which comprises a therapeutically effective amount of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid or a pharmaceutically acceptable salt thereof;

[4] the pharmaceutical composition of item [3], which further comprises a therapeutically effective amount of one or more additional compounds known to be useful in the treatment or prevention of gastrointestinal diseases or the symptoms thereof;

[5] a method for the treatment of gastrointestinal diseases in an animal subject including a mammalian subject, which comprises administering to the animal subject including a mammalian subject 4-{[4-({[4-(2,2,2-trifluoroethoxy)-1,2-benzisoxazol-3-yl]-oxy}methyl)piperidin-1-yl]m ethyl}tetrahydro-2H-pyran-4-carboxylic acid or a pharmaceutically acceptable salt thereof;

[6] the method of item [5], which comprises further administering a therapeutically effective amount of one or more additional compounds known to be useful in the treatment or prevention of gastrointestinal diseases;

[7] a method for the treatment of gastrointestinal diseases, which comprises administering to an animal subject including a mammalian subject in need a therapeutically effective amount of 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid or a pharmaceutically acceptable salt thereof;

[8] the method of item [7], which comprises further administering a therapeutically effective amount of one or more additional compounds known to be useful in the treatment or prevention of gastrointestinal diseases; and

[9] 4-{[4-({[4-(2,2,2-trifluoroethoxy)-1,2-benzisoxazol-3-yl]oxy}methyl)-piperidin-1-yl]methyl}tetrahydro-2H-pyran-4-carboxylic acid or a pharmaceutically acceptable salt thereof for use in the treatment of gastrointestinal diseases in an animal subject including a mammalian subject.

Advantageous Effects of Invention

It has now surprisingly been found that Compound A of this invention which has a strong effects on GI motilities in both upper and lower GI tracts is useful for the treatment of gastrointestinal diseases.

Namely, the present inventors discovered that Compound A of this invention has the desirable property for the treatment of gastrointestinal diseases using the dog gastric emptying model and dog gastrointestinal motility model. Compound A of this invention has also been discovered to have the much stronger (more than 100 times) potency than other 5-TH4 agonist such as cisapride, mosapride, and tegaserod in the models above.

Therefore, Compound A of this invention is useful for the treatment of gastrointestinal diseases.

DESCRIPTION OF EMBODIMENTS

Compound A of this invention for the treatment of gastrointestinal diseases is 4-{[4-({[4-(2,2,2-Trifluoroethoxy)-1,2-benzisoxazol-3-yl]oxy}methyl)piperidin-1l-yl]m ethyl}tetrahydro-2H-pyran-4-carboxylic acid, which is disclosed in WO2006/090224.

Compound A of this invention includes solvates, hydrates, complexes, polymorphs, prodrugs, isomers, and isotopically-labelled compounds.

Also, the present invention provides a pharmaceutical composition for the treatment of gastrointestinal diseases in an animal subject including a mammalian subject, which comprises administering to the subject above a therapeutically effective amount of Compound A or a pharmaceutically acceptable salt thereof.

Further, the present invention also provides a pharmaceutical composition for the treatment of gastrointestinal diseases which comprises a therapeutically effective amount of Compound A or its pharmaceutically acceptable salt together with a pharmaceutically acceptable carrier.

Also, the present invention provides a method for the treatment of gastrointestinal diseases in an animal subject including a mammalian subject, which comprises administering to the subject above in need a therapeutically effective amount of Compound A or a pharmaceutically acceptable salt thereof. Further, the present invention provides a method for the treatment of gastrointestinal diseases in an animal subject including a mammalian subject, which comprises administering to the animal subject including a mammalian subject Compound A or a pharmaceutically acceptable salt thereof. Furthermore, the present invention provides use of Compound A or a pharmaceutically acceptable salt thereof in the manufacture of a medicament for the treatment of gastrointestinal diseases in an animal subject including a mammalian subject.

The term "animal subject," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese.

The term "gastrointestinal diseases" includes GERD, functional dyspepsia, IBS, constipation and other types of gastrointestinal diseases that are associated with the reduced GI motility. The term "gastrointestinal diseases" also includes the clinical symptoms such as heartburn, dyspepsia, nausea and abdominal pain.

The term "treating", as used herein, refers to reversing, alleviating, inhibiting, or preventing the onset or the progression of the disorder or condition to which such term applies, or one or more symptoms of such disorder or condition. The term "treatment" as used herein refers to the act of treating, as "treating" is defined immediately above.

The present invention also includes isotopically-labelled compounds of Compound A, but for the fact that one or more atoms can be replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compound A of the present invention, prodrugs thereof, pharmaceutically acceptable esters thereof and pharmaceutically acceptable salts of the said compound, of said esters or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assay. Tritiated hydrogen, i.e., $^{3}H$, and carbon-14, i.e., $^{14}C$, isotopes are particularly preferred for their ease of presentation and detectability. Further, substitution with heavier isotopes such as deuterium, i.e., $^{2}H$, can afford therapeutic advantage resulting from greater metabolic stability, for example increased in vivo half-life or reduced dosage requirement and, hence, may be preferred in some circumstances. Isotopically labelled compounds of Compound A of this invention and prodrugs thereof can generally be prepared by carrying out the procedure disclosed in the patent publication (WO2006/090224), and by substituting a readily available isotopically labelled reagent for a non-isotopically labelled reagent.

The present invention includes salt forms of Compound A as obtained.

Compound A of the present invention may be capable of forming pharmaceutically acceptable non-toxic cations.

The bases which are used to prepare the pharmaceutically acceptable base addition salts of Compound A are those which form non-toxic base addition salts. The base addition salts can be prepared by conventional procedures.

As Compound A of this invention is a basic compound, they are capable of forming a wide variety of different salts with various inorganic and organic acids.

The acids which are used to prepare the pharmaceutically acceptable acid addition salts of the basic compounds of this invention of Compound A are those which form non-toxic acid addition salts The acid addition salts can be prepared by conventional procedures.

For a review of suitable salts, see Berge S. M. et al., J. Pharm. Sci., 66, 1-19, 1977.

Also included within the scope of this invention are bioprecursors (also called "prodrugs") of Compound A. A bioprecursor of Compound A is a chemical derivative thereof which is readily converted back into the parent compound of Compound A in biological systems. In particular, a bioprecursor of Compound A is converted back to the parent Compound A after the bioprecursor has been administered to, and absorbed by, an animal subject including a mammalian subject, e.g., a human subject.

Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

When Compound A of this invention forms solvates such as hydrates, such solvates are included within the scope of this invention.

For treating or preventing gastrointestinal diseases, a suitable dosage level of Compound A of this invention to an adult human (60 kg/weight) is about 0.0001 to 1000 mg per day, preferably about 0.001 to 100 mg per day, and more preferably about 0.005 to 50 mg per day. The compound may be administered on a regimen of 1 to 4 times per day. In some cases, however, a dosage outside these limits may be used.

Compound A of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., it may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matters or dyes, and, if so desired, emulsifying and/or suspending agents as well, together with such diluents as water, ethanol, propylene glycol, glycerin and various like combinations thereof.

For parenteral administration, solutions of Compound A of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art. Additionally, it is also possible to administer Compound A of the present invention topically when treating inflammatory conditions of the skin and this may preferably be done by way of creams, jellies, gels, pastes, ointments and the like, in accordance with standard pharmaceutical practice.

Also, the present invention provides a pharmaceutical composition for the treatment of gastrointestinal diseases in an animal subject including a mammalian subject, which comprises administering to the subject above a therapeutically effective amount of Compound A or pharmaceutically acceptable salts thereof.

Further, the present invention also provides a pharmaceutical composition for the treatment of gastrointestinal diseases, which comprises a therapeutically effective amount of Compound A or its pharmaceutically acceptable salt together with a pharmaceutically acceptable carrier.

The invention also provides a method of treating gastrointestinal diseases, or preventing or delaying the onset or the progression of gastrointestinal diseases, by administering a therapeutically effective amount of Compound A of this invention or a pharmaceutically acceptable salt thereof to a patient or an animal subject including a mammalian subject in need thereof, wherein gastrointestinal diseases are associated with the reduced GI motility.

In a further aspect, the invention provides the use of Compound A, or a pharmaceutically acceptable salt thereof, in the manufacture of a medicament for treating gastrointestinal diseases, or preventing or delaying the onset or the progression of gastrointestinal diseases.

One embodiment of the present invention is a combination of Compound A and a drug for gastrointestinal diseases. A "combination" according to the invention may be present as a "fix combination" or as a "kit of parts combination". A "fix combination" is defined as a combination wherein the (i) at least one drug for gastrointestinal diseases; and (ii) Compound A are present in one unit. A "kit of parts combination" is defined as a combination wherein the (i) at least one drug for gastrointestinal disease; and (ii) Compound A are present in more than one unit. The components of the "kit of parts combination" may be administered simultaneously, sequentially or separately. The molar ratio of the drug for gastrointestinal diseases to Compound A is used according to the invention in within the range of from 1:100 to 100:1, such as from 1:50 to 50:1 or from 1:20 to 20:1 or from 1:10 to 10:1. The two drugs may be administered separately in the same ratio. Examples of acid secretion inhibiting agents are other 5-HT4 agonists, proton pump inhibitors, H2 receptor antagonists, and drugs for IBS or constipations. These examples are H2 blocking agents such as cimetidine, ranitidine; as well as proton pump inhibitors such as pyridinylmethylsulfinyl benzimidazoles such as omeprazole, esomeprazole, lansoprazole, pantoprazole, rabeprazole or related substances such as leminoprazole.

EXAMPLES

Compounds List:
Compound A.

Example 1

GI motility was assessed by processing the signals from the force transducers implanted in dogs prepared for investigation of motility. Briefly, dogs were anesthetized with isoflurane and the abdominal cavity was opened under aseptic conditions. Extraluminal force transducers (F-12IS, Star Medical, Tokyo) were sutured onto the seromuscular layer of the gastric antrum, the gastric body, the duodenum, and the proximal colon. After the surgery, protective jackets were placed on the dogs and they were housed in individual cages. The dogs were fasted overnight before the experiment and placed in the shield room. The motility was measured with a telemetry system (GTS-800, Star Medical, Tokyo) and data acquired into a personal computer with the acquisition software (Eight Star, Star Medical, Tokyo). After confirmation of interdigestive migrating complex (IMC), the test drugs were administered orally. Gut motility was then recorded more than 5 hours (hrs). To measure the gastric motility quantitatively, motor indexes that represent areas of contractions were calculated. The signals from the force transducer were acquired on a personal computer and analyzed by processing software (Analyze II; StarMedical). In the fasted state, the areas surrounded by the contraction curve and the baseline were determined every 2 hrs after administration. For standardization, the calculated areas were divided by the IMC peak height before administration, and they were used as the motor index (MI). Results are presented as the mean+/− standard error of the mean (S.E.M., N=4-5). Statistical analysis was performed with Dunnett's multiple comparison test using GraphPad Prism (GraphPad Software, Inc.).

Figure 1:
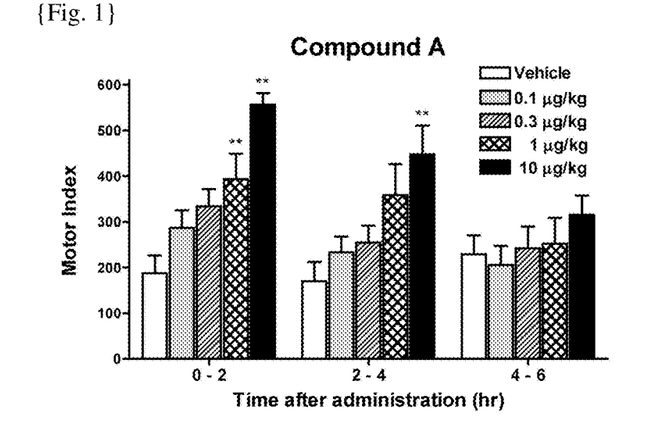
FIG. 1 is a graph showing dose-dependent increase of gastric antral motility following oral administration of Compound A in the fasted state in conscious dogs.
Figure 2:
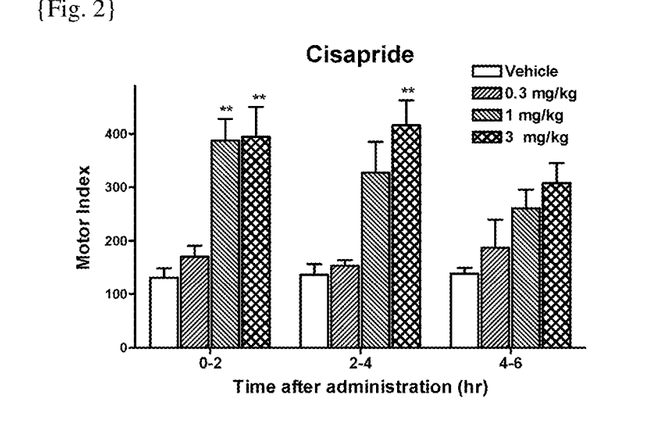
FIG. 2 is a graph showing dose-dependent increase of gastric antral motility following oral administration of cisapride in the fasted state in conscious dogs.
Figure 3:
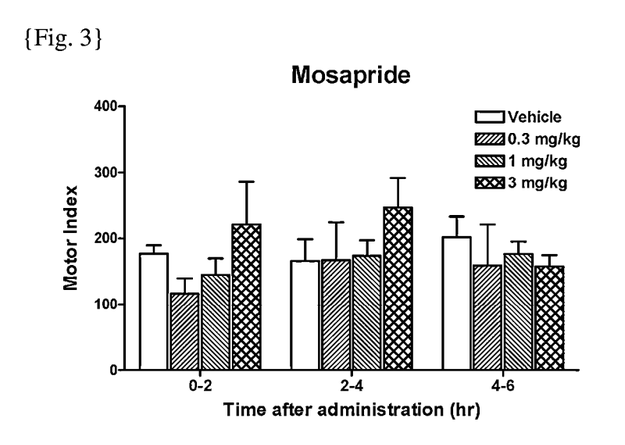
FIG. 3 is a graph showing the effect of mosapride on gastric antral motility in the fasted state in conscious dogs.

Results:

In dogs, Compound A increased the gastric antral motor activity in dose dependent manner (0.1-10 micro g/kg)(FIG. 1). During the 0 to 2 hour period after oral administration of Compound A, the measured change in the MI achieved statistical significance at 1 micro g/kg, which was determined to be the minimum effective dose in this model. Cisapride at the dose of 1 mg/kg significantly increased gastric antral motility (FIG. 2), but mosapride tended to increase the antral motility at 3 mg/kg (FIG. 3). These data of the GI motility experiment are identical for those of published literature (Mikami T. et al., J. Phrmacol. Exp. Ther., 325, 190-199, 2008; Mine Y. et al., J. Phrmacol. Exp.

Ther., 283, 100-1008, 1997.). Compound A is approximately 1000 times more potent than cisapride in enhancing gastric antral motility.

Figure 4:
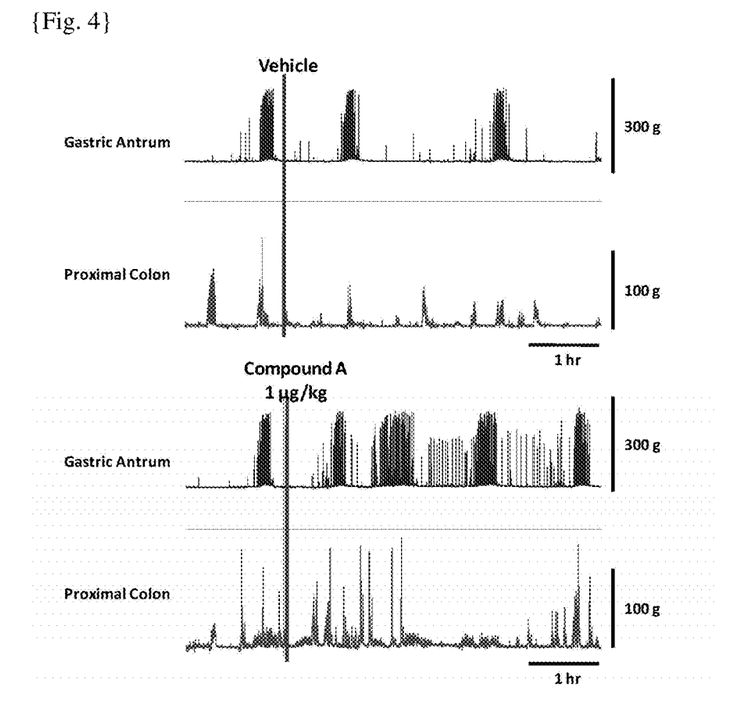
FIG. 4 is a graph showing the increase of gastric antral and proximal colon motility following oral administration of Compound A (1 micro g/kg) in the fasted state in conscious dogs (typical tracing).
Figure 5:
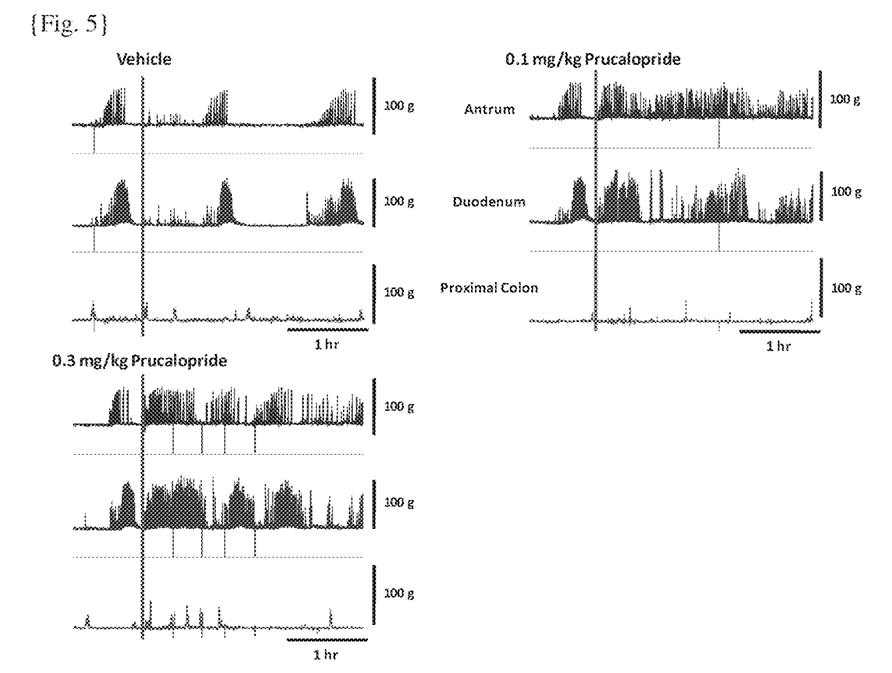
FIG. 5 is a graph showing the effect of prucalopride (0.1, 0.3 mg/kg) on gastric antrum, duodenum, and proximal colon motility in the fasted state in conscious dogs (typical tracings).

In the proximal colon, amplitude and frequency of contractions were enhanced by 1 micro g/kg of Compound A (FIG. 4). Moreover, Compound A facilitated the occurrence of giant migrating contractions after treatment. On the other hand, oral administration of prucalopride (0.1 mg/kg) stimulated gastric antral motility, but did not affect contractions of proximal colon at this dose. Only the high dose treatment (0.3 mg/kg) of prucalopride enhanced the colonic motor activity, but induced excessive gastro-duodenum contractions (FIG. 5).

CONCLUSION

A large population of patients with functional bowel disorders have frequently overlapping symptoms that affect both the upper and lower GI tract. For example, IBS is frequently seen in association with GERD. Compound A is one of the most potent and selective 5-HT4 agonist, exert stimulatory effects on antral and colonic motility at the same dose; there is no tissue specific activity in the gut. These profiles suggest that Compound A could be of valuable and feasible alternative to other prokinetic agents for patients suffering from functional constipation and C-IBS with upper GI symptoms such as dyspepsia or heartburn.

Prucalopride has recently been approved by the European Medicines Agency for the treatment of chronic constipation. In this study in dogs, prucalopride induced excessive gastro-duodenum contractions at the dose that enhance the proximal colon motility, suggesting tissue specific activity. Generally, excessive contractions in the pyrolic ring and duodenum do not lead to the emptying of the stomach.

INDUSTRIAL APPLICABILITY

According to the present invention, Compound A or a pharmaceutically acceptable salt thereof is useful for the treatment of gastrointestinal diseases.

All publications, including but not limited to, issued patents, patent applications, and journal articles, cited in this application are each herein incorporated by reference in their entirety. Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

The invention claimed is:

1. A method for the treatment of gastrointestinal diseases characterized by decreased upper gastrointestinal (GI) motility and decreased lower GI motility by stimulating the upper and lower GI motilities, which comprises administering to an animal subject including a mammalian subject in need thereof 4-{[4-({[4-(2,2,2-trifluoroethoxy)-1,2-benzisoxazol-3-yl]oxy}methyl)piperidin-1-yl]methyl}tetrahydro-2H-pyran-4-carboxylic acid or a pharmaceutically acceptable salt thereof in an amount which is therapeutically effective to stimulate both upper and lower GI motilities at the same dose of about 0.005 to 50 mg per day/60 kg weight of the subject being treated.

2. The method of claim 1, which comprises further administering a therapeutically effective amount of one or more additional compounds known to be useful in the treatment or prevention of gastrointestinal diseases.

3. A method of stimulating both upper and lower GI motilities in a mammalian subject suffering from functional bowel disorders characterized by decreased upper GI motility and decreased lower GI motility comprising administering 4-{[4-({[4-(2,2,2-trifluoroethoxy)-1,2-benzisoxazol-3-yl]oxy}-methyl)piperidin-1-yl]methyl}tetrahydro-2H-pyran-4-carboxylic acid or a pharmaceutically acceptable salt thereof in an amount which is therapeutically effective to stimulate both upper and lower GI motilities at the same dose of about 0.005 to 50 mg per day/60 kg weight of the subject being treated.

4. The method according to claim 3, wherein the animal subject including a mammalian subject in need is a patient suffering from dyspepsia and heartburn with lower gastrointestinal symptoms.

5. The method according to claim 4, wherein the lower gastrointestinal symptoms are selected from the group consisting of functional constipation and constipation-predominant irritable bowel syndrome (C-IBS).

6. The method according to claim 3, wherein the functional bowel disorders are functional constipation with upper gastrointestinal symptoms or constipation-predominant irritable bowel syndrome (C-IBS) with upper gastrointestinal symptoms.

7. The method according to claim 6, wherein upper gastrointestinal symptoms are selected from the group consisting of dyspepsia and heartburn.

8. The method according to claim 3, which comprises further administering a therapeutically effective amount of one or more additional compounds selected from the group consisting of other 5-HT4 agonists, proton pump inhibitors, H2 receptor antagonists, and drugs for irritable bowel syndrome or constipations.

9. The method according to claim 8, wherein H2 receptor antagonists are selected from the group consisting of cimetidine and ranitidine; and the proton pump inhibitors are selected from the group consisting of omeprazole, esomeprazole, lansoprazole, pantoprazole, rabeprazole and leminoprazole.

10. The method according to claim 3, wherein the functional bowel disorders are (1) functional constipation with dyspepsia or heartburn, or (2) constipation-predominant irritable bowel syndrome (C-IBS) with dyspepsia or heartburn.

* * * * *

UNITED STATES PATENT AND TRADEMARK OFFICE
CERTIFICATE OF CORRECTION

PATENT NO. : 10,137,113 B2
APPLICATION NO. : 14/006550
DATED : November 27, 2018
INVENTOR(S) : Takahashi Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this
Fourth Day of February, 2020

Andrei Iancu
*Director of the United States Patent and Trademark Office*